United States Patent

Farge et al.

[11] 4,188,203
[45] Feb. 12, 1980

[54] HERBICIDAL AND PHYTOHORMONAL AMIDOXIMES

[75] Inventors: Daniel Farge, Thiais; Jean Leboul, Gip; Yves Le Goff, Bretigny, Orge; Gilbert Poiget, Thiais, all of France

[73] Assignee: Philagro, France

[21] Appl. No.: 928,371

[22] Filed: Jul. 27, 1978

Related U.S. Application Data

[63] Continuation-in-part of Ser. No. 772,215, Sep. 10, 1976, Pat. No. 4,116,974.

[30] Foreign Application Priority Data

Sep. 11, 1975 [FR] France .............................. 75 27884
Jul. 8, 1976 [FR] France .............................. 76 21717
Jul. 28, 1977 [FR] France .............................. 77 24114

[51] Int. Cl.² .................... C07D 333/26; A01N 9/12
[52] U.S. Cl. .............................. 71/90; 549/77; 549/75
[58] Field of Search .................. 260/329 R, 332.2 A; 71/90, 329 AM

[56] References Cited

PUBLICATIONS

Eloy, F. et al., "The Chemistry of Amidoximes and Related Compounds," Chemical Reviews, vol. 62, pp. 155–183 (1962).

*Primary Examiner*—Bernard Helfin
*Assistant Examiner*—L. Hendriksen
*Attorney, Agent, or Firm*—Robert E. Burns; Emmanuel J. Lobato; Bruce L. Adams

[57] ABSTRACT

1—Amidoxime derivatives. The amidoximes correspond to the formula:

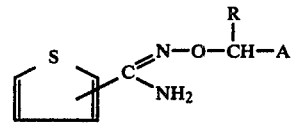

in which: R represents a hydrogen atom or an alkyl radical containing from 1 to 4 carbon atoms and A represents a cyano group or a radical of the general formula:

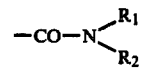

in which $R_1$ and $R_2$, which are identical or different, each represent a hydrogen atom, an alkyl radical containing from 1 to 4 carbon atoms, an optionally substituted phenyl radical or an amino radical which is itself optionally substituted. These compounds can be used in agriculture as phytohormones and herbicides.

8 Claims, No Drawings

HERBICIDAL AND PHYTOHORMONAL AMIDOXIMES

This is a continuation-in-part of our copending U.S. application Ser. No. 722,215 filed Sept. 10, 1976, now U.S. 4,116,974.

BACKGROUND OF THE INVENTION

The parent patent application Ser. No. 772,215, now U.S. 4,116,974 relates to new derivatives of amidoximes of the formula:

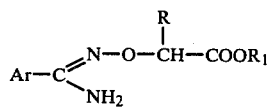
(I)

their preparation, the compositions in which they are present, and the treatments carried out with these compositions.

In the general formula (I), R represents a hydrogen atom or an alkyl radical containing 1 to 4 carbon atoms, or a phenyl radical, $R_1$ represents a hydrogen atom or an alkyl radical containing 1 to 4 carbon atoms, or a metal atom, and Ar represents a phenyl radical substituted by 1 to 3 substituents which may be identical or different and are chosen from amongst halogen atoms and the following radicals: alkyl containing 1 to 4 carbon atoms, hydroxyl, alkoxy of which the alkyl part contains 1 to 4 carbon atoms, alkylthio of which the alkyl part contains 1 to 4 carbon atoms, alkylsulphinyl of which the alkyl part contains 1 to 4 carbon atoms, alkylsulphonyl of which the alkyl part contains 1 to 4 carbon atoms, trifluoromethyl, trifluoromethoxy, trifluoromethylthio, carboxyl, alkoxycarbonyl of which the alkyl part contains 1 to 4 carbon atoms, nitro, amino, alkylamino of which the alkyl part contains 1 to 4 carbon atoms, dialkylamino of which each alkyl part contains 1 to 4 carbon atoms, acylamino of which the acyl part contains 1 to 4 carbon atoms, alkoxycarbonylamino of which the alkyl part contains 1 to 4 carbon atoms, azido, alkanoyl containing 1 to 4 carbon atoms, sulphamoyl optionally substituted at the nitrogen by one or two alkyl groups, in which case each alkyl part contains 1 to 4 carbon atoms, or phenyl, or represents an aromatic heterocyclic radical with 5 chain members which contains an atom of oxygen, sulphur or nitrogen as the heteroatom and is optionally substituted by a halogen atom, an alkyl radical containing 1 to 4 carbon atoms, an alkoxy radical of which the alkyl part contains 1 to 4 carbon atoms, an alkylthio radical of which the alkyl part contains 1 to 4 carbon atoms or a phenylalkyl radical of which the alkyl part contains 1 to 4 carbon atoms and is itself optionally substituted.

SUMMARY OF THE INVENTION

The present application relates to new amidoxime derivatives according to the abovementioned general formula I.

It also relates to the preparation of these compounds as well as to the compositions in which they are present.

The compounds according to the present application correspond to the formula:

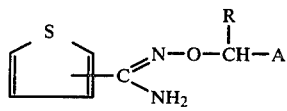
formula II in which: R represents a hydrogen atom or an alkyl radical containing from 1 to 4 carbon atoms and A represents a cyano group or a radical of the general formula:

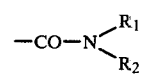

in which $R_1$ and $R_2$, which are identical or different, each represent a hydrogen atom, an alkyl radical containing from 1 to 4 carbon atoms, an optionally substituted phenyl radical or an amino radical which is itself optionally substituted.

DESCRIPTION OF THE INVENTION

When R represents an alkyl radical, the compounds according to the formula II exist in two optically isomeric forms which are also included in the present invention.

The preferable compounds of the present invention correspond to the formula:

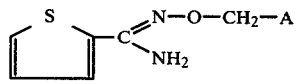
formula III in which: A represents a cyano radical or a radical of the formula:

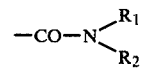

in which $R_1$ and $R_2$, which are identical or different, each represent a hydrogen atom, an alkyl radical containing from 1 to 4 carbon atoms, a phenyl radical, or an amino radical which is itself optionally substituted by one or two identical or different radicals chosen from amongst alkyl radicals containing from 1 to 4 carbon atoms and the phenyl radical.

The compounds according to the present application show remarkable properties which render them particularly useful in the field of agriculture.

When used at doses of between 0.1 and 100 g/hl of water, they exhibit phytohormonal properties which are similar to those of indolylacetic acid and phenoxyacetic acid derivatives. Essentially, they are useful for assisting the setting of fruit on certain plants (tomatoes), preventing the shedding of leaves or fruit, or also increasing root formation.

When used at doses of between 0.5 and 10 kg/ha, the compounds according to the present application show herbicidal properties, in particular against dicotyledon plants, both in pre-emergence and in post-emergence application.

The compounds according to the invention can be prepared in accordance with several processes which also form the subject of the present application.

1—The compounds according to formula II in which A represents a group

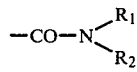

can be obtained, in accordance with a process which is in itself known, by the action of ammonia, or an amine of the general formula $NHR_1R_2$ in which $R_1$ and $R_2$ have the same meaning as in formula II, on a compound of the formula:

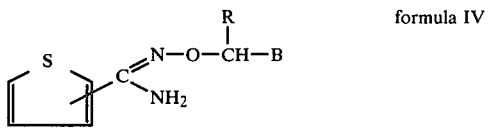

formula IV which is optionally in the form of hydrochloride. In the formula IV, R has the same meaning as in formula II and B represents either the radical —CO—O—$R_3$, in which $R_3$ represents an alkyl radical containing from 1 to 4 carbon atoms, or the radical —COCl.

When B represents the radical —CO—O—$R_3$, the reaction is carried out at a temperature of between about 15° C. and 100° C., optionally under pressure and either in an organic solvent medium, for example in alcoholic or aqueous-alcoholic solution, or in the absence of solvent when the reactants are liquid under the reaction conditions.

The preparation of compounds corresponding to formula IV in which B represents the radical —CO—O—$R_3$ has been described in the parent application Ser. No. 772,215, now U.S. 4,116,974.

When B represents the radical —CO—Cl, the reaction is carried out by reacting the hydrochloride of a compound of formula IV with a compound of the formula $NHR_1R_2$, at a temperature of between about 15 and 50° C. and either in an inert solvent medium or in the absence of solvent when the reactants are liquid under the reaction conditions.

The compounds of formula IV in which B represents a radical —COCl can be obtained, in accordance with the conventional processes for preparing acid chlorides, from the corresponding acids, the preparation of which has been described in parent application Ser. No. 722,215, now U.S. 4,116,974.

2—The compounds according to formula II in which A represents a cyano radical can be obtained, in accordance with a process which is in itself known, by reacting an amidoxime of the formula:

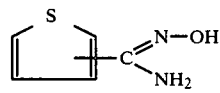

with a halogenonitrile of the formula:

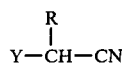

in which R has the same meaning as in formula II and Y represents a halogen atom, in the presence of an alkaline condensation agent such as a quaternary ammonium hydroxide, sodium hydroxide or potassium hydroxide, in an aqueous-organic solvent medium such as a mixture of dimethylformamide and water, and at a temperature which can vary from about 15° C. to 80° C.

The following examples illustrate the invention without however limiting it.

EXAMPLE 1: Preparation of 0-(carbamoylmethyl)-thiophene-2-carboxamidoxime (compound 1)

A solution of 0-(ethoxycarbonylmethyl)-thiophene-2-carboxamidoxime (20 g) in methanol (200 cc) is saturated with ammonia, whilst keeping the mixture at a temperature of less than 40° C. Thereafter, the mixture is stirred for 16 hours and the solvent is then distilled under reduced pressure (20 mm Hg) at a temperature of about 35° C.

The residue is taken up with water (100 cc) and the crystals obtained are filtered off, washed with water (3×50 cc) and dried at a temperature of about 40° C.

0-(Carbamoylmethyl)-thiophene-2-carboxamidoxime (11 g), which melts at 199° C., is thus obtained. After recrystallisation from acetonitrile, the pure product melts at 199° C.

EXAMPLE 2: Preparation of 0-(hydrazinocarbonylmethyl)-thiophene-2-carboxamidoxime (compound 2)

A solution of 0-(ethoxycarbonylmethyl)-thiophene-2-carboxamidoxime (20 g) in ethanol (200 cc) is added dropwise, in the course of 50 minutes, to hydrazine hydrate (200 cc), heated to 95° C., and the reaction mixture is then kept at a temperature of between 85° C. and 95° C. for 1 hour.

The mixture is then concentrated under reduced pressure (20 mm Hg and then 1 mm Hg) at a temperature of about 60° C. in order to drive off the ethanol and the major part of the hydrazine hydrate, the residue is then taken up with water (200 cc) and the crystals are filtered off and washed with water (3×50 cc).

After standing for 16 hours, the mother liquors provide a second crop of white crystals which are collected by filtration and washed with water (2×10 cc).

The two crops are combined and dried together. 0-(Hydrazinocarbonylmethyl)-thiophene-2-carboxamidoxime (10 g) is thus obtained. After recrystallisation from acetonitrile (20 parts), the product melts at 156° C.

EXAMPLE 3

By following the same procedure as in Example 2, using the appropriate starting materials, the following compounds were prepared:

| No. of compound | Formula | Yield | M.p. (°C.) |
| --- | --- | --- | --- |
| 3 | ![structure with S, NH2, NOCH2CON(CH3)2] | 49.5% | 120 |

-continued

| No. of compound | Formula | Yield | M.p. (°C.) |
|---|---|---|---|
| 4 | ![structure] thiophene-C(=NOCH₂CONHCH₃)NH₂ | 64.0% | 153 |
| 5 | ![structure] thiophene-C(=NO—CH₂—CO—NH—NH—C₆H₅)NH₂ | 49.5% | 169 |

EXAMPLE 4:

Preparation of 0-(anilinocarbonylmethyl)-thiophene-2-carboxamidoxime (compound no. 6)

0-(Chloroformylmethyl)-thiophene-2-carboxamidoxime (10.2 g. is added in small portions to aniline (30 cc) and the reaction mixture is allowed to stand for several hours. Ether (150 cc) is added and the precipitate of aniline hydrochloride is filtered off and washed with ether (2×50 cc).

The filtrate is concentrated under reduced pressure (20 mm Hg) at a temperature of about 30° C., and then under a pressure of 1 mm Hg at a temperature of 90° C. 0-(Anilinocarbonylmethyl)-thiophene-2-carboxamidoxime (10.9 g) is thus obtained in the form of an oil which slowly solidifies.

After recrystallization from acetonitrile (20 cc), the pure product melts at 123° C.

EXAMPLE 5

By following the procedure of Example 4, using appropriate starting materials, 0-(N,N-dimethylhydrazinocarbonylmethyl)-thiophene-2-carboxamidoxime (compound no. 7) was prepared.

M.p.—139° C.
Yield—40%

Example 6: Preparation of 0-(cyanomethyl)-thiophene-2-carboxamidoxime (compound no. 8)

Thiophene-2-carboxamidoxime (14.2 g) is added to an aqueous solution (84.2 cc) containing 17.5% of tetraethylammonium hydroxide; after 5 hours at a temperature of about 20° C., the water is evaporated off under reduced pressure (1 mm Hg) at a temperature of about 25° C. and the residue obtained is then redissolved in dimethylformamide (100 cc).

The solution is cooled to a temperature of about 5° C., chloroacetonitrile (11.3 g) is run therein and the mixture is allowed to return to a temperature of about 20° C. After 16 hours, dimethylformamide (about 70 cc) is distilled under reduced pressure (1 mm Hg) at a temperature of about 25° C. and water (100 cc) is then added. After having stirred the mixture for 2 hours, the crystals are filtered off, washed with water (3×20 cc) and dried; these crystals are dissolved in ethyl acetate (150 cc), decolorized with animal charcoal and dried over calcined magnesium sulphate.

After filtering and evaporating off the solvent, 0-(cyanomethyl)-thiophene-2-carboxamidoxime (10.1 g), which melts at 96° C., is obtained.

After recrystallization from methanol, the pure crystals melt at 96° C.

EXAMPLE 7: Phytohormonal activity

A product (10 parts) resulting from the condensation of ethylene oxide with octylphenol at a rate of 10 molecules of ethylene oxide per molecule of octylphenol is added to a solution of the active material to be tested (25 parts) in a mixture (65 parts) of equal parts of toluene and acetophenone. The solution is used after dilution with water to the desired concentration.

1—Propagation of tomato leaves

The second and third leaves are removed from tomato stems of the Marmande variety having 5 to 6 leaves. The petiole of each leaf is dipped over a length of 2 to 3 cm into the solution to be studied which is contained in a test tube. Eight days after the start of the experiment, the percentage of rooted leaves and the mean number of roots per rooted leaf are evaluated.

| | Concentration of active material mg/liter | % of rooted leaves | Mean number of roots per rooted leaf |
|---|---|---|---|
| Control | 0 | 50 | 5 |
| Compound no. 1 | 0.01 | 100 | 10 |
| | 0.1 | 100 | 20 |
| Compound no. 2 | 0.01 | 100 | 15 |
| | 0.1 | 100 | 15 |
| Compound no. 5 | 0.01 | 50 | 5 |
| | 0.1 | 100 | 8 |
| Compound no. 8 | 0.01 | 100 | 45 |
| | 0.1 | 85 | 8 |

2-Setting of fruit of tomatoes

The solutions to be studied are sprayed onto the first and second flower trusses of tomato stems of the Marmande variety when 2 to 3 flowers of each truss are on the point of opening. Before the treatment, the number of flower buds on each truss is counted. All the other trusses which subsequently form on the treated plants are removed as they appear. One month after the treatment, the number of fruits which have formed is counted and compared with the results obtained on control plants treated with an aqueous solution containing the same wetting agent.

| | Concentration in g/hl | $\dfrac{\text{Total number of fruits}}{\text{Number of treated flowers}} \times 100$ |
|---|---|---|
| Control | 0 | 30 |
| Compound no. 1 | 3 | 80 |
| Compound no. 2 | 3 | 80 |
| Compound no. 3 | 3 | 40 |

EXAMPLE 8: Herbicidal activity

A solution or dispersion of the active material having the following composition is used:

| | |
|---|---|
| active material to be tested | 400 mg |
| acetone (solvent) | 5 ml |
| oxyethyleneated sorbitol monooleate containing 20 mols of ethylene oxide (wetting agent) | 50 mg |
| distilled water containing 0.1% of the product resulting from the condensation of 10 mols of ethylene oxide with one mol of octylphenol....q.s.p. | 40 ml |

This solution or dispersion is then diluted with distilled water in order to obtain the desired concentration.

Seeds of various species, namely wheat (Triticum sativum), lentil (Lens culinaris), radish (Raphanus sativus), sugar beet (Beta vulgaris) and slender foxtail (Alopecurus agrestis), are sown in plastic pots (180 cc capacity) containing to a height of 6 cm a mixture composed of ⅓ of clean earth, ⅓ of vegetable mould and ⅓ of river sand, at a rate of about 30 seeds per pot. 2 pots of wheat and four pots of the other species are used for each concentration of product.

For the purpose of a post-emergence treatment, the sowing is carried out in a greenhouse one week before the start of the experiment, so that the small plants are at the following stage at the time of treatment:

| | |
|---|---|
| wheat and foxtail | 3 leaves |
| lentils | 3 leaves |
| beet and radish | 2 well-developed cotyledon leaves. |

The treatment is carried out by spraying the solution or suspension of the product, the pots being placed on a pot-turner. Each pot is given 1 cc of the solution. The doses of the product to be studied are 1 and 8 kg/ha.

In pre-emergence testing, the seeded surface of the pots is allowed to dry and then covered to a depth of 1 cm with the same earth mixture. The pots are watered twice a day by sprinkling.

In post-emergence testing, the treated small plants are allowed to dry. The earth mixture is moistened by placing the base of the pots in a tray containing water.

In both cases, the pots are kept in a greenhouse (22° to 24° C., 70 to 80% relative humidity) under artificial light which provides 5,000 to 6,000 Lux at the level of the plants, for 17 consecutive hours per day.

Three weeks after the start of the treatment, the number of small plants in each pot is counted and their height is measured.

The results are expressed in percentage destruction relative to the control plant.

The results are summarized in the table which follows. Percentages equal to 0 and 100% indicate that there is respectively complete selectivity and complete destruction of the species in question.

| No. of compound | Dose Kg/ha | Pre-emergence | | | | | Post-emergence | | | | |
|---|---|---|---|---|---|---|---|---|---|---|---|
| | | Wheat | Lentil | Radish | Beet | Foxtail | Wheat | Lentil | Radish | Beet | Foxtail |
| 1 | 1 | 30 | 100 | 40 | 50 | 50 | 0 | 60 | 0 | 0 | 0 |
| | 8 | 70 | 100 | 100 | 100 | 75 | 0 | 100 | 60 | 25 | 25 |
| 2 | 1 | 30 | 100 | 60 | 50 | 75 | 0 | 50 | 0 | 0 | 0 |
| | 8 | 70 | 100 | 100 | 90 | 100 | 0 | 100 | 60 | 25 | 25 |
| 3 | 1 | 0 | 0 | 0 | 0 | 0 | 0 | 0 | 0 | 0 | 11 |
| | 8 | 30 | 100 | 0 | 50 | 80 | 0 | 0 | 0 | 0 | 0 |
| 5 | 1 | 30 | 100 | 0 | 80 | 75 | 0 | 0 | 0 | 0 | 50 |
| | 8 | 50 | 100 | 100 | 100 | 90 | 0 | 70 | 100 | 70 | 50 |
| 6 | 1 | 20 | 100 | 30 | 100 | 50 | 0 | 0 | 0 | 0 | 0 |
| | 8 | 60 | 100 | 100 | 100 | 100 | 0 | 70 | 20 | 100 | 25 |
| 7 | 1 | 20 | 100 | 30 | 80 | 50 | 0 | 0 | 0 | 0 | 0 |
| | 8 | 30 | 100 | 100 | 100 | 75 | 0 | 70 | 0 | 0 | 0 |
| 8 | 1 | 20 | 100 | 80 | 80 | 75 | 0 | 100 | ° | 0 | 20 |
| | 8 | 75 | 100 | 100 | 100 | 100 | 0 | 100 | + | 0 | 40 |

For their use in practice, the compounds according to the invention are rarely employed by themselves but in the form of agricultural compositions which also form the subject of the present application.

These compositions generally comprise, in addition to the active material according to the invention, a carrier and/or a surface-active agent which are compatible with the active material and can be used in agriculture. The proportion of active product in these compositions can be between 0.005 and 95% by weight.

The term "carrier," for the purpose of the present description, denotes an organic or inorganic, natural or synthetic material with which the active material is combined in order to facilitate its application to the plant, to seeds or to the soil, or in order to facilitate its transport or handling. The carrier can be solid (clays, natural or synthetic silicates, resins, waxes, solid fertilisers or the like) or fluid (water, alcohols, ketones, petroleum fractions, chlorohydrocarbons or liquefied gases).

The surface-active agent can be an emulsifier, dispersing agent or wetting agent, each of which can be ionic or non-ionic. Examples which may be mentioned are salts of polyacrylic acids and of ligninsulphonic acids, and condensates of ethylene oxide with fatty alcohols, fatty acids or fatty amines.

The compositions according to the invention can be prepared in the form of wettable powders, dusting powders, solutions, emulsifiable concentrates, emulsions, suspension concentrates and aerosols.

The wettable powders are usually prepared so that they contain from 20 to 95% by weight of active material, and they usually contain, in addition to a solid carrier, from 0 to 5% of a wetting agent, from 3 to 10% by weight of a dispersing agent and, where necessary, from 0 to 10% by weight of one or more stabilizers and/or other additives such as penetrating agents adhesives or anti-caking agents, dyestuffs and the like.

By way of example, the composition of a wettable powder is given, the percentages being expressed by weight:

| | |
|---|---|
| active material (compound no. 1) | 50% |
| calcium lignosulphonate (deflocculant) | 5% |
| isopropyl naphthalenesulphonate (wetting agent) | 1% |
| anti-caking silica | 5% |
| filler (kaolin) | 39% |

The dusting powders are usually prepared in the form of a dust concentrate having a composition which is similar to that of a wettable powder but without the dispersing agent, and they are diluted on site with a complementary amount of solid carrier so that a composition is obtained which usually contains from 0.5 to 10% by weight of active material.

The emulsifiable concentrates which can be applied by spraying usually contain, in addition to the solvent and where necessary, a co-solvent, from 10 to 50% by weight/volume of emulsifiers and from 0 to 20% by weight/volume of suitable additives such as stabilizers, penetrating agents, corrosion inhibitors and dyestuffs and adhesives.

By way of example, the composition of an emulsifiable concentrate is given, the amounts being expressed in g/liter:

| | |
|---|---|
| active material (compound no. 2) | 400 g/l |
| dodecyl benzenesulphonate | 24 g/l |
| nonylphenol containing 10 molecules of ethylene oxide | 16 g/l |
| cyclohexanone | 200 g/l |
| aromatic solvent | q.s.p. 1 liter |

The suspension concentrates, which can also be applied by spraying, are prepared so that a stable fluid product is obtained which does not form a deposit, and they usually contain from 10 to 75% by weight of active material, from 0.5 to 15% by weight of surface-active agents, from 0.1 to 10% by weight of anti-sedimentation agents such as protective colloids and thixotropic agents, from 0 to 10% by weight of suitable additives such as anti-foam agents, corrosion inhibitors, stabilizers, penetrating agents and adhesives, and, as the carrier, water or an organic liquid in which the active material is essentially insoluble; certain solid organic materials or inorganic salts can be dissolved in the carrier to assist in preventing the sedimentation or to act as anti-freeze agents for the water.

Aqueous dispersions and aqueous emulsions, for example compositions obtained by diluting a wettable powder or an emulsifiable concentrate, according to the invention, with water, also fall within the general scope of the present invention. These emulsions can be of the water-in-oil type or of the oil-in-water type and they can have a thick consistency such as that of a "mayonnaise."

For a so-called "ultra-low volume" application, entailing spraying as very fine droplets, solutions in organic solvents are prepared which contain from 70 to 95% of active material.

The compositions according to the invention can contain other ingredients, for example protective colloids, adhesives or thickeners, thixotropic agents, stabilizers or sequestering agents as well as other known active materials having pesticidal properties, in particular insecticidal or fungicidal properties.

We claim:
1. A compound of the formula:

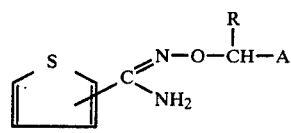

in which: R represents a hydrogen atom or an alkyl radical containing from 1 to 4 carbon atoms and A represents a cyano group or a radical of the general formula:

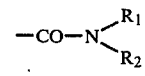

in which $R_1$ and $R_2$, which are identical or different, each represent a hydrogen atom, an alkyl radical containing from 1 to 4 carbon atoms, an optionally substituted phenyl radical or an amino radical which is itself optionally substituted.

2. A compound according to claim 1 of the formula:

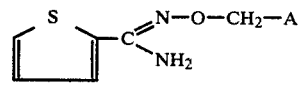

in which: A represents a cyano radical or a radical of the formula:

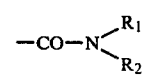

in which $R_1$ and $R_2$, which are identical or different, each represent a hydrogen atom, an alkyl radical containing from 1 to 4 carbon atoms, a phenyl radical, or an amino radical which is itself optionally substituted by one or two radicals chosen from amongst alkyl radicals containing from 1 to 4 carbon atoms and the phenyl radical.

3. A phytohormonal composition which contains, as the active material, at least one compound according to claim 1 in combination with at least one inert carrier and/or one surfaceactive agent for agricultural use.

4. Composition according to claim 3, wherein its proportion of active material is between 0.005 and 95% by weight.

5. Process for phytohormonal treatment which comprises treating the crops with a composition according to either claim 3 or 4.

6. A herbicidal composition which contains, as the active material, an effective amount of at least one compound according to claim 1 in combination with at least one inert carrier and/or one surface-active agent for agricultural use.

7. A composition according to claim 6 wherein its proportion of active material an effective amount of is between 0.005 and 95% by weight.

8. A process for herbicidal treatment which comprises treating the crops with a composition according to either claim 6 or 7.

* * * * *